US00PP11678P

United States Patent [19]

Trees

[11] Patent Number: Plant 11,678

[45] Date of Patent: Dec. 12, 2000

[54] GERANIUM PLANT NAMED 'BALFANPISH'

[75] Inventor: Scott C. Trees, Nipomo, Calif.

[73] Assignee: Ball Floraplant, a division of Ball Horticultural Co., West Chicago, Ill.

[21] Appl. No.: 09/255,653

[22] Filed: Feb. 20, 1999

[51] Int. Cl.[7] ..... A01H 5/00

[52] U.S. Cl. ..... Plt./329

[58] Field of Search ..... Plt./329, 325, 328

*Primary Examiner*—Howard J. Locker
*Assistant Examiner*—Wendy A Baker
*Attorney, Agent, or Firm*—C. A. Whealy

[57] ABSTRACT

A new and distinct cultivar of Geranium plant named 'Balfanpish', characterized by its numerous semi-double lavender colored flowers; upright growth habit; basal branching and vigorous; and dark green leaves with a faint zonation pattern.

1 Drawing Sheet

BACKGROUND OF THE INVENTION

The present invention relates to a new and distinct cultivar of Geranium plant, botanically known as *Pelargonium×hortorum,* and hereinafter referred to by the cultivar name Balfanpish.

The new Geranium is a product of a planned breeding program conducted by the Inventor in Arroyo Grande, Calif. The objective of the breeding program was to develop new cultivars with freely-branching growth habit, dark green-colored foliage, uniform flowering, round umbels, and interesting flower and foliage colors.

The new Geranium originated from a cross made by the Inventor of the proprietary *Pelargonium×hortorum* selection BFP-1198, as the male, or pollen parent, with the proprietary *Pelargonium×hortorum* selection BFP-790 as the female, or seed parent. The cultivar Balfanpish was discovered and selected by the Inventor as a flowering plant within the progeny of the stated cross in a controlled environment in Arroyo Grande, Calif., in December, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balfanpish'. These characteristics in combination distinguish 'Balfanpish' as a new and distinct cultivar:

1. Numerous semi-double lavender colored flowers.
2. Upright growth habit.
3. Basal branching and vigorous.
4. Dark green leaves with a faint zonation pattern.

The new Geranium can be compared to the cultivar, BSR-284 Pink cultivar, disclosed in U.S. Plant Pat. No. 8,287. However, in side-by-side comparisons conducted in Arroyo Grande, Calif., plants of the new Geranium differ from plants of the cultivar BSR-284 Pink cultivar in the following characteristics:

1. Plants of the new Geranium are more vigorous than plants of the cultivar BSR-284 Pink cultivar.

2. Plants of the new Geranium have shorter internodes than plants of the cultivar BSR-284 Pink cultivar.

3. Leaves of plants of the new Geranium are darker green with a less distinct zonation pattern than leaves of plants of the cultivar BSR-284 Pink cultivar.

4. Plants of the new Geranium have fewer flowers per umbel than plants of the cultivar BSR-284 Pink cultivar.

5. Plants of the new Geranium and the cultivar BSR-284 Pink cultivar differ in flower color.

6. Sepal color of plants of the new Geranium is maroon at the base whereas sepal color of plants of the cultivar BSR-284 Pink cultivar is green.

A detailed comparison of plants of the cultivar Balfanpish and the cultivar BSR-284 Pink cultivar, as grown side by side, appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'Balfanpish'. Flower and foliage colors in the photograph may appear different from the actual colors due to light reflectance.

DETAILED BOTANICAL DESCRIPTION

The cultivar Balfanpish has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20 to 22° C., night temperatures about 18 to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium×hortorum* cultivar Balfanpish.

Parentage:

*Male parent.*—Proprietary *Pelargonium×hortorum* selection BFP-1198.

*Female parent.*—Proprietary *Pelargonium×hortorum* selection BFP-790.

Propagation:

*Type cutting.*—Terminal cuttings.

*Time to initiate roots.*—About 7 days at 18° C.

*Time to develop roots.*—About 21 days at 18° C.

*Rooting habit.*—Fibrous and freely branching.

Plant description:

*General appearance.*—Upright growth habit. Appropriate for 10 and 12.5-cm containers.

*Crop time.*—Starting with a rooted cutting, about eight weeks are required to produced a finished flowering plant in 10-cm container.

*Growth and branching habit.*—Vigorous and basal branching with about two lateral branches at the base. Pinching, that is, removal of the terminal apex, is usually not required.

*Plant height* (*to top of foliage*).—About 11 to 12 cm.

*Plant width.*—About 16 to 18 cm.

*Lateral branches.*—Length: about 5 to 7 cm. Internode length: About 8 to 15 mm. Color: 146A; streaks, 183B.

*Foliage description.*—Leaves simple, generally symmetrical, abundant, opposite. Quantity of leaves per lateral branch: About 7 to 10. Length: About 4 to 5 cm. Width: About 7 to 7.5 cm. Shape: Reniform. Apex: Rounded. Base: Cordate. Margin: Crenate. Venation: Palmate. Texture: Both surfaces pubescent; velvety. Color: Young and fully expanded foliage, upper surface: 147A with faint zonation pattern, darker than 147A in color and about 2 cm in width. Young and fully expanded foliage, lower surface: Between 147A and 147B. Venation, upper surface: 146D. Venation, lower surface: 146A. Petiole: Length: About 4 to 5.3 cm. Diameter: About 2 to 3 mm. Color: 146A; streaks, 183B.

Flower description:

*Flower type and habit.*—Lavender colored flowers. Freely and continuously flowering. Flowers aranged in round umbels arising from apical leaf axils. Umbels displayed above or beyond the foliage. At full flowering, usually about three or four open umbels and about two or three developing umbels per plant. Flowers semi-double and round. Umbels persistent. Not fragrant.

*Flowering season.*—Year-round under greenhouse conditions. In the garden, flowering is continuous from spring until fall.

*Umbels.*—Number of flowers per umbel: About 30 to 40. Diameter: About 10.5 tp 11.5 cm. Height: About 6 to 7 cm.

*Flowers.*—Diameter: About 4 to 5 cm. Depth (height): About 8 to 10 mm.

*Flower buds.*—Length: About 1.4 to 1.6 cm. Diameter: About 7 to 8 mm. Shape: Round.

*Petals.*—Quantity: About 5 or 6 petals and about 2 or 3 irregularly-shaped petaloids per flower. Arrangement: Imbricate. Length: About 2 to 2.7 cm. Width: About 2 to 2.5 cm. Shape: Obovate. Apex: Rounded. Base: Attenuate. Margin: Entire. Texture: Smooth, iridescent. Color: When opening and fully opened, upper surface: Background, 75B; base, 73D which produces a lighter pink "eye". Upper petals have a larger area of lighter pink, 73D, than lower petals. When opening and fully opened, lower surface: One solid color, between 73D and 75D.

*Sepals.*—Quantity: About 5, not imbricate. Length: About 1.1 to 1.2 cm. Width: About 3 to 4 mm. Shape: Lanceolate. Apex: Pointed. Margin: Entire. Texture: Pilose. Color: Upper surface: Base, 183A, to 146B at apex. Lower surface: Base, 183C, to 146B at apex.

*Peduncle* (*umbel stem*).—Length: About 14 to 16 cm. Angle: Erect. Strength: Strong. Texture: Pubescent. Color: Young, 187A; mature, 146C.

*Pedicel* (*individual flower stem*).—Length: About 3 to 4 cm. Angle: Upright to outward. Strength: Moderately strong. Texture: Pubescent. Color: 185C over green background.

*Reproductive organs.*—Androecium: Anther size: About 2 to 2.5 mm. Anther color: 72C. Pollen color: 39A. Gynoecium: Ovary color: Green.

Disease resistance: Resistance to pathogens common to Pelargonium has not been observed.

Seed developement: See production has not been observed.

CHART A

| CHARACTERISTIC | 'BALFANPISH' | 'BSR-284 PINK CULTIVAR' |
|---|---|---|
| PLANT HEIGHT (to top of foliage) | About 11 to 12 cm | About 10 to 11 cm |
| PLANT WIDTH | About 16 to 18 cm | About 15 to 17 cm |
| VIGOR | Vigorous | Moderately vigorous |
| INTERNODE LENGTH | About 8 to 15 mm | About 1.5 to 2 cm |
| LEAF COLOR, FULLY EXPANDED, UPPER SURFACE | 147A | 147B |
| LEAF COLOR, FULLY EXPANDED, LOWER SURFACE | Between 147A and 147B | 147C |
| LEAF ZONATION PATTERN | Faint zonation pattern | Distinct zonation pattern |
| NUMBER OF FLOWERS PER UMBEL | About 30 to 40 | ABout 50 to 60 |
| PETAL COLOR, FULLY OPENED, UPPER SURFACE | Background, 75B; base, 73D which produces a lighter pink "eye". Upper petals have a larger area of lighter pink, 73D, than lower petals. | 68B; base, 155D. Upper petals have larger white area venation of 68C |
| PETAL COLOR, FULLY OPENED, LOWER SURFACE | Between 73D and 75D | 68D; venation, 68C |
| PEDUNCLE COLOR | Young, 187A Mature, 146C | 141C |
| SEPAL COLOR, UPPER SURFACE | Base, 183A; apex, 146B | 143C |
| SEPAL COLOR, LOWER SURFACE | Base, 183C; apex, 146B | 143C |
| POLLEN COLOR | 39A | 33A |

It is claimed:

1. A new and distinct cultivar of Geranium plant named 'Balfanpish', as illustrated and described.

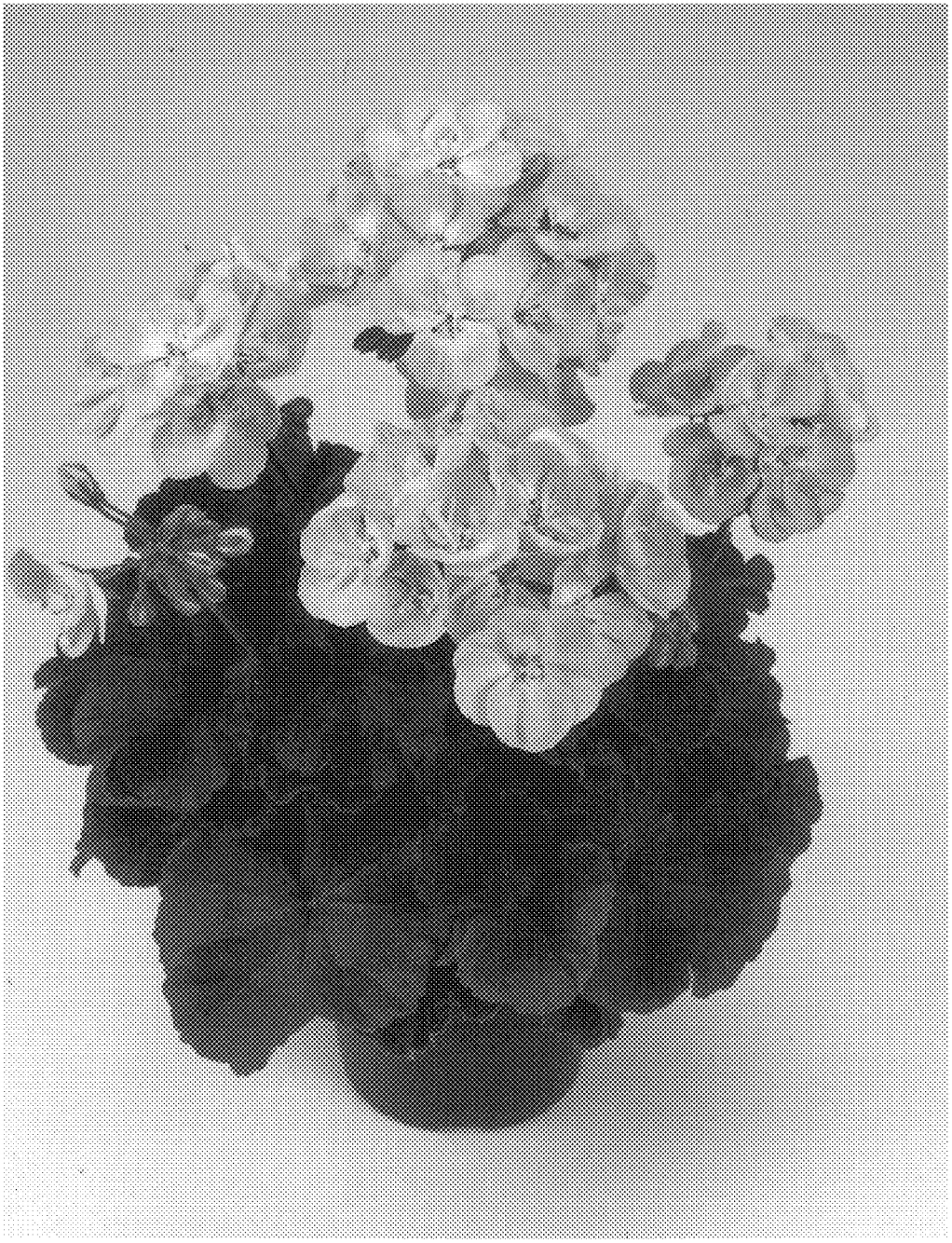

* * * * *